United States Patent
Dieing et al.

(10) Patent No.: US 6,355,231 B1
(45) Date of Patent: Mar. 12, 2002

(54) USE OF CATIONIC COPOLYMERS OF UNSATURATED ACIDS AND N-VINYLIMIDAZOLIUM SALTS IN COSMETIC HAIR FORMULATIONS

(75) Inventors: Reinhold Dieing; Peter Hössel, both of Schifferstadt; Axel Sanner, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/168,104

(22) Filed: Oct. 8, 1998

(30) Foreign Application Priority Data

Oct. 16, 1997 (DE) .......................... 197 45 637

(51) Int. Cl.[7] .......................... A61K 7/06; C08F 22/40; C08F 26/06
(52) U.S. Cl. ............... 424/70.1; 424/70.11; 424/70.16; 424/70.122; 526/262; 526/265
(58) Field of Search ............... 424/70.1, 70.11, 424/70.16, 70.122; 526/262, 265

(56) References Cited

U.S. PATENT DOCUMENTS

| 5,580,494 | A | | 12/1996 | Sandhu et al. ............... 510/125 |
|---|---|---|---|---|
| 5,674,478 | A | * | 10/1997 | Dodd et al. ................. 424/70.1 |
| 5,773,545 | A | * | 6/1998 | Schade et al. ............... 526/262 |
| 5,980,878 | A | * | 6/1998 | Torgerson et al. ...... 424/70.122 |
| 5,846,924 | A | * | 12/1998 | Detering et al. ............ 510/475 |

FOREIGN PATENT DOCUMENTS

| CA | 2164554 | 6/1996 |
|---|---|---|
| EP | 100890 | 2/1984 |
| EP | 246580 | 11/1987 |
| EP | 715843 | 6/1996 |
| WO | 94/06403 | 3/1994 |
| WO | 94/06409 | 3/1994 |

* cited by examiner

*Primary Examiner*—Thurman K. Page
*Assistant Examiner*—S. Tran
(74) *Attorney, Agent, or Firm*—Keil & Weinkauf

(57) ABSTRACT

Cationic polymers obtainable by free-radically initiated copolymerization of (a) from 60 to 99% by weight, based on the overall amount of all monomers, of a substituted or unsubstituted and quaternized or nonquaternized 1-vinylimidazole, (b) from 1 to 40% by weight of an acid which contains a polymerizable double bond, or of salts of such an acid, and (c) from 0 to 30% by weight of a further free-radically copolymerizable monomer, percentages by weight being based in each case on the overall amount of all monomers, and quaternization of the polymer if a nonquaternized 1-vinylimidazole was employed as monomer a) are used as active ingredients in cosmetic hair formulations such as shampoos.

5 Claims, No Drawings

USE OF CATIONIC COPOLYMERS OF UNSATURATED ACIDS AND N-VINYLIMIDAZOLIUM SALTS IN COSMETIC HAIR FORMULATIONS

The present invention relates to the use of cationic polymers obtainable by free-radically initiated copolymerization of monomer mixtures comprising
(a) from 60 to 99% by weight of a 1-vinylimidazole or of a quaternized 1-vinylimidazole,
(b) from 1 to 40% by weight of an unsaturated acid or of salts of such an acid,
(c) from 0 to 30% by weight of a further free-radically copolymerizable monomer
and optional subsequent quaternization of the polymer, as active ingredients in cosmetic hair formulations, especially as conditioning agents in shampoos.

The purpose of shampoos for hair is to free the hair from dirt. In addition to this cleansing effect, modern shampoos perform conditioning functions as well. The conditioning effect is achieved by virtue of the presence of conditioning agents in the shampoo composition.

Examples of conditioning agents employed in shampoos are, in particular, silicones and cationic polymers. The silicones have the disadvantage that they are generally insoluble in water and so must be stabilized in the shampoo formulation by means of dispersants. These additives are undesirable. In addition, silicones show a strong accumulation effect; in other words, they attach to the hair and are not completely removed by washing. After a certain time, the hair feels unpleasantly heavy.

The cationic polymers used as conditioning agents in shampoos, such as cationic cellulose derivatives, however, form—together with the anionic surfactants in the shampoo formulation—surfactant-polymer complexes which are insoluble in water when the polymers have a high charge density. Consequently, it is common to employ cationic polymers having a low charge density, which are hence soluble in the formulation.

Since, however, cationic polymers with a high charge density have a greater affinity for the hair, it is desirable to employ highly charged polymers in shampoos. Then, however, the surfactant-polymer complexes are insoluble in the formulation, and the latter has to be stabilized by adding dispersing auxiliaries.

For instance, WO 94/06403 proposes the use of, inter alia, copolymers of N-vinylpyrrolidone and 3-methyl-1-vinylimidazolium salts of high charge density, in combination with further water-insoluble conditioning agents, in shampoo formulations. The formulations are stabilized accordingly using dispersants. WO 94/06409 and U.S. Pat. No. 5,580,494, furthermore, describe shampoo compositions based on an alpha-olefinsulfonate as detergent and on a cationic copolymer of high charge density, for example a copolymer of N-vinylpyrrolidone and 3-methyl-1-vinylimidazolium salts, as conditioning agent. Here too, however, the formulations must be stabilized by adding dispersing auxiliaries.

EP-A 246 580, moreover, discloses the use of quaternized vinylimidazole copolymers with various other monomers, but not including polymerizable unsaturated acids, as hair conditioning agents. The polymers described therein have the disadvantage that if the proportion of quaternized vinylimidazole monomers is small there is little effect in the presence of anionic surfactants whereas if the proportion of the quaternized vinylimidazole is high the resulting dispersions are not stable.

It is an object of the present invention to find cationic polymers of high charge density which can be employed without addition of dispersing auxiliaries in shampoo formulations comprising anionic surfactants.

We have found that this object is achieved by the use of cationic copolymers obtainable by free-radically initiated copolymerization of
(a) from 60 to 99% by weight, preferably from 65 to 95% by weight and, with particular preference, from 70 to 90% by weight of a substituted or unsubstituted 1-vinylimidazole or of a quaternized 1-vinylimidazole,
(b) from 1 to 40% by weight, preferably from 5 to 35% by weight and, with particular preference, from 10 to 30% by weight of an acid containing a polymerizable double bond, or of salts of such an acid, and
(c) from 0 to 30% by weight, preferably from 0 to 20% by weight and, with particular preference, from 0 to 10% by weight of a further free-radically copolymerizable monomer
and subsequent quaternization of the polymer if a nonquaternized 1-vinylimidazole is employed as monomer (a), as active ingredients in cosmetic hair formulations, especially as conditioning agents in shampoos.

The quaternization of the polymers in this context is generally conducted so as to give complete quaternization of the vinylimidazole units. Alternatively, it is possible to perform only a partial quaternization, for example up to 80% and, preferably, more than 90% quaternization.

Suitable monomers (a) are 1-vinylimidazole or its derivatives of the formula I

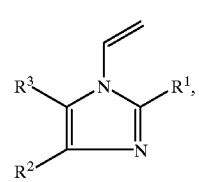

in which $R^1$ to $R^3$ independently are hydrogen, $C_1C_4$-alkyl or phenyl.

1-vinylimidazole and 2-methyl-1-vinylimidazole are preferred.

To quaternize the compounds of the formula I use is made appropriately of conventional methods of adding on alkyls, aralkyls or hydroxyalkyls, examples of such methods being reaction with alkyl halides of 1 to 24 carbons, such as methyl chloride, methyl bromide, methyl iodide, ethyl chloride, ethyl bromide, propyl chloride, hexyl chloride, dodecyl chloride, lauryl chloride and with benzyl halides, especially benzyl chloride and benzyl bromide. Further particularly suitable quaternizing agents are dialkyl sulfates, especially dimethyl sulfate or diethyl sulfate. The quaternization of the base monomers or polymers can also be conducted with alkylene oxides, such as ethylene oxide or propylene oxide, in the presence of acids.

Preferred quaternizing agents are: methyl chloride, dimethyl sulfate and diethyl sulfate.

Monomers (b) are, for example, unsaturated carboxylic acids of 2 to 8 carbons, such as acrylic, methacrylic, dimethylacrylic, ethacrylic, crotonic, itaconic, methylenemalonic and maleic acid and maleic monoesters, fumaric acid and fumaric monoesters. Also suitable are unsaturated sulfonic acids, such as vinylsulfonic or acrylamidomethylpropanesulfonic acid, and also unsaturated phosphonic acids, an example of which is vinylphosphonic acid. The unsaturated acids can be either in the form of the free acids or in partly or fully neutralized form in the copolymers. The monomers are neutralized if appropriate with alkali metal hydroxides, such as sodium hydroxide or potassium hydroxide, or with ammonia or amines.

Preferred monomers (a) are acrylic, methacrylic and acrylamidomethylpropanesulfonic acid.

Suitable monomers (c) are all those which are copolymerizable with the monomers (a) and (b). Suitable examples are N-vinyllactams, such as N-vinylpiperidone, N-vinylpyrrolidone or N-vinylcaprolactam, and also N-vinylacetamide, N-methyl-N-vinylacetamide, acrylamide, methacrylamide, N,N-dimethylacrylamide, N-methylolmethacrylamide, N-vinylformamide, N-vinyloxazolidone, N-vinyltriazole, hydroxyalkyl (meth) acrylates, such as hydroxyethyl (meth)acrylate and hydroxypropyl (meth)acrylates, or alkyl ethylene glycol (meth) acrylates having 1 to 50 ethylene glycol units in the molecule. Also suitable are dialkylaminoalkyl acrylates and methacrylates, such as dimethylaminoethyl methacrylate, or dialkylaminoalkylacrylamides and methacrylamides, an example being dimethylaminopropylmethacrylamide.

Mention should also be made of $C_1$-$C_{24}$-, especially $C_1C_{10}$-alkyl esters of acrylic or methacrylic acid, examples of which are methyl acrylate, methyl methacrylate, ethyl acrylate, ethyl methacrylate, tert-butyl acrylate, tert-butyl methacrylate, isobutyl acrylate, n-butyl acrylate, and acrylamides such as N-tert-butylacrylamide and N-tert-octylacrylamide. It is also possible to employ vinyl carboxylates such as vinyl acetate or vinyl propionate, for example.

The monomers of groups (a) to (c) can in each case be employed individually or in a mixture with further monomers from the same group.

Particular preference is given to copolymers of
  (a) from 70 to 90% by weight of 3-methyl-1-vinylimidazoleium chloride or the corresponding methyl sulfate and
  (b) from 10 to 30% by weight of acrylic acid, methacrylic acid or acrylamidomethylpropanesulfonic acid or salts thereof.

The polymers can be prepared by the conventional techniques of the free-radically initiated polymerization; for example, by solution, emulsion, suspension, precipitation, inverted suspension or inverted emulsion polymerization, without the employable techniques being restricted to these.

They are preferably prepared by solution polymerization in solvents such as water, methanol, ethanol, isopropanol or mixtures thereof. The amounts of monomers and solvents are judiciously chosen so as to give solutions with a strength of from 15 to 60% by weight.

Polymerization takes place normally at from 20 to 130° C. and at atmospheric or the autogenous pressure.

Initiators which can be employed for the free-radical polymerization are the water-soluble and water-insoluble peroxo and/or azo compounds customary for this purpose, examples being alkali metal or ammonium peroxodisulfates, dibenzoyl peroxide, tert-butyl perpivalate, tert-butyl-per-2-ethylhexanoate, di-tert-butyl peroxide, tert-butyl hydroperoxide, azobisisobutyronitrile, azobis(2-amidinopropane)dihydrochloride or 2,2"-azobis(2-methylbutyronitrile). Also suitable are initiator mixtures or redox initiator systems, such as ascorbic acid/iron (II) sulfate/sodium peroxodisulfate, tert-butyl hydroperoxide/ sodium sulfite, tert-butyl hydroperoxide/sodium hydroxymethanesulfinate. The initiators can be employed in the customary amounts, examples being amounts from 0.05 to 5% by weight, based on the amount of monomers to be polymerized.

The K values are measured in accordance with Fikentscher, Cellulosechemie 13 (1932) 58–64, at 25° C. in 1% strength solutions in 0.5 molar sodium chloride solution and range from 10 to 200, preferably from 20 to 150.

The polymers to be used in accordance with the invention are generally suitable as conditioning agents in cosmetic formulations, especially in cosmetic hair formulations such as hair treatment compositions, hair lotions, hair rinses, hair emulsions, treatment fluids for damaged ends, equalizing agents for permanent waves, hot oil treatment preparations, conditioners, setting lotions or hairsprays.

Depending on the field of use the cosmetic hair formulations can be applied in the form of a spray, foam, gel, gel spray or mousse.

In addition to the polymers of the invention and appropriate solvents, such as water or water/alcohol mixtures, the cosmetic hair formulations may also include customary cosmetics additives, such as emulsifiers, preservatives, perfume oils, care substances such as panthenol, collagen, vitamins, protein hydrolyzates, stabilizers, pH regulators, colorants and further customary additives.

The polymers to be used in accordance with the invention can also be blended with conventional hair-cosmetics polymers if specific properties are to be established. Examples of suitable conventional hair-cosmetics polymers are anionic polymers. Anionic polymers of this kind are homo- and copolymers of acrylic and methacrylic acid or salts thereof; copolymers of acrylic acid and acrylamide and salts thereof; sodium salts of polyhydroxycarboxylic acids; water-soluble or water-dispersible polyesters, polyurethanes and polyureas. Particularly suitable polymers are copolymers of tert-butyl acrylate, ethyl acrylate, methacrylic acid (eg. Luvimer® 100P, 36D, 30E, MAE), copolymers of N-tert-butylacrylamide, ethyl acrylate, acrylic acid (Ultrahold® 8, strong), copolymers of vinyl acetate, crotonic acid, vinyl propionate (eg. Luviset® CAP), maleic anhydride copolymers, unmodified or reacted with alcohols; anionic polysiloxanes, such as carboxyfunctional polysiloxanes, and copolymers of vinylpyrrolidone, tert-butyl acrylate and methacrylic acid (eg. Luviskol® VBM).

Especially preferred anionic polymers are acrylates having an acid number of greater than or equal to 120, and copolymers of t-butyl acrylate, ethyl acrylate and methacrylic acid.

Further suitable hair-cosmetics polymers that can be used together with the polymers that are to be employed in accordance with the invention are, for example, cationic polymers bearing the INCI designation Polyquaternium, such as copolymers of vinylpyrrolidone/N-vinylimidazolium salts (Luviquat® FC, Luviquat® HM, Luviquat® MS), copolymers of N-vinylpyrrolidone/ dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (Polyquaternium 4 and 10), acrylamide copolymers (Polyquaternium 7).

Also suitable as further constituents in hair-cosmetics formulations are neutral polymers, such as polyvinylpyrrolidones, copolymers of N-vinylpyrrolidone and vinyl acetate and/or vinyl propionate, polysiloxanes, polyvinylcaprolactam and copolymers with N-vinylpyrrolidone, polyethyleneimines and their salts, polyvinylamines and their salts, cellulose derivatives, salts of polyaspartic acid, and derivatives.

To establish particular properties it is possible for the formulations to comprise, in addition and in small amounts, conditioning substances based on silicone compounds. Suitable examples are polyalkylsiloxanes, polyarylsiloxanes, polyarylalkylsiloxanes, polyether siloxanes or silicone resins.

The polymers to be used in accordance with the invention are particularly suitable for use as conditioning agents in shampoo formulations. Accordingly, the invention also provides shampoo formulations comprising the copolymers defined above.

In the shampoo formulations it is possible to use all anionic, neutral, amphoteric or cationic surfactants which are normally employed in shampoos. These are usually anionic surfactants as base surfactants, and amphoteric and nonionic surfactants as cosurfactants.

The shampoo formulations generally contain from 2 to 50% by weight of surfactants, preferably from 5 to 40% by weight and, with particular preference, from 8 to 30% by weight.

Examples of suitable anionic surfactants are alkyl sulfates, alkyl ether sulfates, alkylsulfonates, alkylarylsulfonates, alkylsuccinates, alkylsulfosuccinates, N-alkylsarcosinates, acyltaurates, acylisethionates, alkyl phosphates, alkyl ether phosphates, alkyl ether carboxylates, alpha-olefinsulfonates, especially the alkali metal and alkaline earth metal salts, eg. sodium, potassium, magnesium, calcium, and also ammonium and triethanolamine salts. The alkyl ether sulfates, alkyl ether phosphates and alkyl ether carboxylates can have from 1 to 10 ethylene oxide or propylene oxide units, preferably from 1 to 3 ethylene oxide units, in the molecule.

Examples of suitable such compounds are sodium lauryl sulfate, ammonium lauryl sulfate, sodium lauryl ether sulfate, ammonium lauryl ether sulfate, sodium lauroyl sarcosinate, sodium oleyl succinate, ammonium laurylsulfosuccinate, sodium dodecylbenzenesulfonate, triethanolamine dodecylbenzenesulfonate.

Examples of suitable amphoteric surfactants are alkyl betaines, alkylamidopropyl betaines, alkyl sulfobetaines, alkyl glycinates, alkyl carboxyglycinates, alkyl amphoacetates or propionates, alkyl amphodiacetates or dipropionates.

It is possible, for example, to employ cocodimethylsulfopropyl betaine, lauryl betaine, cocamidopropyl betaine or sodium cocamphopropionate.

Examples of suitable nonionic surfactants are the reaction products of aliphatic alcohols or alkylphenols having 6 to 20 carbons in the linear or branched alkyl chain with ethylene oxide and/or propylene oxide. The amount of alkylene oxide is from about 6 to 60 mol per mole of alcohol. Also suitable are alkylamine oxide, mono- or dialkylalkanolamides, fatty acid esters or polyethylene glycols, alkyl polyglycosides or sorbitol ether esters.

The shampoo formulations may additionally comprise customary cationic surfactants, such as quaternary ammonium compounds, an example of which is cetyltrimethylammonium chloride.

The polymers to be used in accordance with the invention are usually employed in amounts of from 0.01 to 5% by weight, preferably from 0.05 to 2% by weight, based in each case on the finished shampoo.

It is also possible to employ further cationic polymers which are customary in shampoos, examples being copolymers of acrylamide and dimethyldiallylammonium chloride (Polyquaternium 7), cationic cellulose derivatives (Polyquaternium 10), guarhydroxypropyltrimethylammonium chloride (INCI: hydroxypropyl guar hydroxypropyltrimonium chloride), copolymers of N-vinylpyrrolidone and quaternized N-vinylimidazole (Polyquaternium 16, 44, 46) and others.

The shampoo formulations may also comprise thickeners, such as sodium chloride, PEG-55, propylene glycol oleate or PEG-120 methyl glucose dioleate, and preservatives, further active ingredients and auxiliaries, and water.

A) Preparing the Polymers

EXAMPLE 1

80 g of methacrylic acid and 173 g of water were mixed and the mixture was adjusted to a pH of 7 with 50% strength sodium hydroxide solution. Then 533 g of a 60% strength aqueous solution of 3-methyl-l-vinylimidazoleium chloride (feedstream 1) were added. A stirred apparatus with nitrogen flushing was charged with 70 g of water, 100 g of feedstream 1 and 5 g of feedstream 2, consisting of 3 g of 2,2"-azobis(2-amidinopropane)dihydrochloride and 75 g of water. This initial charge was heated to 60° C., and feedstreams 1 and 2 were metered in over 4 hours in each case. The temperature was then raised to 70° C. and a further 2 g of 2,2'-azobis(2-amidinopropane)dihydrochloride in 75 ml of water were added. Stirring was continued at 70° C. for 1 hour, after which a viscous solution having a solids content of 41.6% and a K value of 56 was obtained.

EXAMPLE 2

100 g of methacrylic acid and 280 g of water were mixed and the mixture was adjusted to a pH of 7.2 with 50% strength sodium hydroxide solution. Then 500 g of a 60% strength aqueous solution of 3-methyl-1-vinylimidazolium chloride (feedstream 1) were added. A stirred apparatus with nitrogen flushing was charged with 100 g of water, 100 g of feedstream 1 and 5 g of feedstream 2, consisting of 3 g of 2,2'-azobis(2-amidinopropane)dihydrochloride and 60 g of water. This initial charge was heated to 60OC, and feedstreams 1 and 2 were metered in over 4 hours in each case. The temperature was then raised to 70° C. and a further 2 g of 2,2'-azobis(2-amidinopropane)dihydrochloride in 75 ml of water were added. Stirring was continued at 70° C. for 1 hour, after which a viscous solution having a solids content of 41.6% and a K value of 56 was obtained.

EXAMPLE 3

120 g of methacrylic acid and 320 g of water were mixed and the mixture was adjusted to a pH of 7 with 50% strength sodium hydroxide solution. Then 445 g of a 60% strength aqueous solution of 3-methyl-1-vinylimidazolium chloride (feedstream 1) were added. A stirred apparatus with nitrogen flushing was charged with 70 g of water, 100 g of feedstream 1 and 5 g of feedstream 2, consisting of 3 g of 2,2'-azobis(2-amidinopropane)dihydrochloride and 75 g of water. This initial charge was heated to 60° C., and feedstreams 1 and 2 were metered in over 4 hours in each case. The temperature was then raised to 70° C. and a further 2 g of 2,2'-azobis(2-amidinopropane)dihydrochloride in 75 ml of water were added. Stirring was continued at 70° C. for 1 hour, after which a viscous solution having a solids content of 39.8% and a K value of 57 was obtained.

EXAMPLE 4

60 g of methacrylic acid, 20 g of acrylamidomethylpropanesulfonic acid and 280 g of water were mixed and the mixture was adjusted to a pH of 7 with 50% strength sodium hydroxide solution. Then 533 g of a 60% strength aqueous solution of 3-methyl-1-vinylimidazolium chloride (feedstream 1) were added. A stirred apparatus with nitrogen flushing was charged with 100 g of water, 96 g of feedstream 1 and 5 g of feedstream 2, consisting of 3 g of 2,2'-azobis (2-amidinopropane)dihydrochloride and 60 g of water. This initial charge was heated to 60° C., and feedstreams 1 and 2 were metered in over 4 hours in each case. The temperature was then raised to 70° C. and a further 2 g of 2,2'-azobis (2-amidinopropane)dihydrochloride in 75 ml of water were added. Stirring was continued at 70° C. for 1 hour, after which a viscous solution having a solids content of 36.6% and a K value of 53 was obtained.

EXAMPLE 5

60 g of methacrylic acid and 200 g of water were mixed and the mixture was adjusted to a pH of 7 with 50% strength sodium hydroxide solution. Then 755 g of a 60% strength aqueous solution of 3-methyl-1-vinylimidazolium methyl sulfate (feedstream 1) were added. A stirred apparatus with nitrogen flushing was charged with 110 g of water, 107 g of feedstream 1 and 6.3 g of feedstream 2, consisting of 3 g of 2,2'-azobis(2-amidinopropane)dihydrochloride and 60 g of water. This initial charge was heated to 60° C., and feedstreams 1 and 2 were metered in over 4 hours in each case. The temperature was then raised to 70° C. and a further 2 g of 2,2'-azobis(2-amidinopropane)dihydrochloride in 60 ml of water were added. Stirring was continued at 70° C. for 1 hour, after which a viscous solution having a solids content of 33.0% and a K value of 42 was obtained.

B) Using the Polymers as Conditioning Agents

EXAMPLES 6 to 8

Subsequently, 3 shampoos formulated as shown below were prepared using the polymers from Examples 1 to 4, and their hair-cosmetic properties were determined.

EXAMPLES 9 to 10
(Comparative Experiments)

3 shampoos formulated as shown below were prepared but using customary commercial cationic polymers.

Shampoo formulation for Examples 6 to 10 in Table 1:

| | |
|---|---|
| Sodium lauryl ether sulfate | 10.0% by weight |
| Cocamidopropyl betaine | 4.0% by weight |
| Polymer (from Example 1, 2, 4 and comparative) | 0.5% by weight |
| Water | ad 100% by weight |

Test Methods
a) Wet Combability

A tensile tester is used to determine the combing force required to draw a comb through a crest of hair. The decrease in combing force is calculated as follows (the greater the value, the better the shampoo).

% decrease in combing force=100(1−Ay/Ao)

Ay=Combability after treatment with the test shampoo (see Examples)
Ao=Combability after treatment with shampoo without polymer (control)

b) Foam Creaminess

Subjective evaluation with a rating scale from 1 (very good) to 3 (poor).

Both the combability of the hair and the foam creaminess are influenced by the nature and amount of the polymer.

c) Stability of the Shampoo Formulations

Shampoo formulations in accordance with the above composition were tested for their stability. Following incorporation by stirring into the surfactant mixture, the polymers of Example 1 to 5 form stable white dispersions which show no precipitation even after several months.

TABLE 1

Performance tests with the above test shampoo

| Shampoo Example No. | Preparation Example No. or commercial product (comparative) | Decreasing combing force 0.5% polymer | Foam creaminess (rating) |
|---|---|---|---|
| 6 | 1 | 49% | 1 |
| 7 | 2 | 39% | 1 |
| 8 | 4 | 48% | 1 |
| 9 | Polyquaternium 7 | 24% | 2 |
| 10 | Polyquaternium 10 | 29% | 2 |

Examples 6 to 8 clearly show the outstanding properties of the compositions with polymers to be used in accordance with the invention relative to known compositions (Examples 9 and 10).

We claim:

1. A shampoo comprising as conditioning agent, from 0.01 to 5% by weight, based on the finished shampoo, of cationic copolymers obtained by free-radically initiated copolymerization of a mixture of monomers consisting essentially of (a) from 60 to 99% by weight, based on the overall amount of all monomers, of a substituted or unsubstituted and quaternized or nonquaternized 1-vinylimidazole, (b) from 1 to 40% by weight of an acid which contains a polymerizable double bond, or of salts of such an acid, and (c) from 0 to 30% by weight of a further free-radically copolymerizable monomer selected from the group consisting of n-vinyllactams, N-vinylacetamide, N-methyl-N-vinylacetamide, acrylamide, methacrylamide, N,N-dimethylacrylamide, N-methylolmethacrylamide, N-vinylformamide, N-vinyloxazolidone, N-vinyltriazole, hydroxyalkyl (meth)acrylates, alkyl ethylene glycol (meth)acrylates having 1 to 50 ethylene glycol units in the molecule, dialkylaminoalkyl acrylates and methacrylates, dialkylaminoalkylacrylamides and -methacrylamides, $C_1$–$C_{24}$-alkyl esters of acrylic or methacrylic acid, and vinyl carboxylates, percentages by weight being based in each case on the overall amount of all monomers, and quaternization of the polymer if nonquaternized 1-vinylimidazole was employed as monomer a).

2. A shampoo as defined in claim 1, comprising as conditioning agent cationic copolymers having a K value, measured as a 1% strength solution in 0.5 molar sodium chloride solution, of from 10 to 200, obtained by free-radically initiated copolymerization of a mixture of (a) from 60 to 99% by weight of a 1-vinylimidazole of the formula I

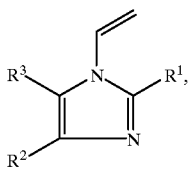

in which $R^1$, $R^2$ and $R^3$ independently are hydrogen, alkyls of 1 to 4 carbons or phenyl, and which 1-vinylimidazole is quaternized, if appropriate, by adding on alkyl radicals of 1 to 24 carbons, aralkyl radicals of 7 to 30 carbons or hydroxyalkyl radicals of 2 to 24 carbons, (b) from 1 to 40% by weight of an acid containing polymerizable double bonds, or of salts of such an acid, and (c) from 0 to 30% by weight of a further free-radically copolymerizable monomer, and subsequent quaternization of the polymer if a nonquaternized 1-vinylimidazole was employed as monomer a), by adding on an alkyl of 1 to 24 carbons, a hydroxyalkyl of 2 to 24 carbons or an aralkyl of 7 to 30 carbons.

3. A shampoo as defined in claim 1 comprising as conditioning agent cationic polymers having a K value, measured as a 1% strength solution in 0.5 molar sodium chloride solution, from 20 to 150, obtained by free-radically initiated copolymerization of a mixture of (a) from 65 to 95% by weight of a 1-vinylimidazole of the formula I as set forth in claim 2, (b) from 5 to 35% by weight of an acid which contains a polymerizable double bond and has 2 to 8 carbon atoms, selected from the group consisting of ba) $\alpha,\beta$-unsaturated carboxylic acids,
bb) unsaturated sulfonic acids and
bc) unsaturated phosphonic acids, and (c) from 0 to 20% by weight of a further free-radically copolymerizable monomer and quaternization of the copolymers with alkyl halides or dialkyl sulfates of 1 to 24 carbons, aralkyl halides of 7 to 30 carbons or alkylene oxides of 2 to 24 carbons.

4. A shampoo as defined in claim 1 comprising as conditioning agent cationic copolymers, wherein the constituent (a) is 1-vinylimidazole or 2-methyl-1-vinylimidazole and the constituent (b) is acrylic, methacrylic or acrylamidomethylpropane-sulfonic acid and the quaternization has been carried out with methyl chloride, dimethyl sulfate or diethyl sulfate.

5. A shampoo as claimed in claim 1, wherein said monomer (c) is selected from the group consisting of N-vinylpiperidone, N-vinylpyrrolidone, N-vinylcaprolactam, N-vinylacetamide, N-methyl-N-vinylacetamide, acrylamide, methacrylamide, N,N-dimethylacrylamide, N-methylolmethacrylamide, N-vinylformamide, N-vinyloxazolidone, N-vinyltriazole, hydroxyethyl (meth)acrylate, hydroxypropyl (meth)acrylate, dimethylaminoethyl methacrylate, dimethylaminopropylmethacrylamide, methyl acrylate, methyl methacrylate, ethyl acrylate, ethyl methacrylate, tert-butyl acrylate, tert-butyl methacrylate, isobutyl acrylate, n-butyl acrylate, N-tert-butylacrylamide and N-tert-octylacrylamide, vinyl acetate and vinyl propionate.

* * * * *